US00PP32209P2

(12) United States Plant Patent
Koppe

(10) Patent No.: US PP32,209 P2
(45) Date of Patent: Sep. 15, 2020

(54) ***BEGONIA* PLANT NAMED 'KROUTWH01'**

(50) Latin Name: ***Begonia boliviensis* X *Begonia* x *tuberhybrida***
Varietal Denomination: KROUTWH01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/602,491

(22) Filed: Oct. 17, 2019

(51) Int. Cl.
*A01H 5/02* (2018.01)
*A01H 6/18* (2018.01)

(52) U.S. Cl.
USPC ..... Plt./343
CPC ..... *A01H 6/18* (2018.05)

(58) Field of Classification Search
USPC ..... Plt./343
CPC ..... A01H 5/02
See application file for complete search history.

(56) References Cited

PUBLICATIONS

PLUTO UPOVROM Plant Variety Database 20200408 Citation for 'Kroutwh01' as per QZ PBR 20183101; Feb. 16, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Begonia* plant named 'KROUTWH01', characterized by its broadly upright and mounded plant habit; moderately vigorous growth habit; moderately freely branching habit; dark green-colored leaves; large single-type white-colored flowers variably blushed with red purple that are positioned above and beyond the foliar plane; and continuous flowering throughout the summer.

2 Drawing Sheets

Figure 1:
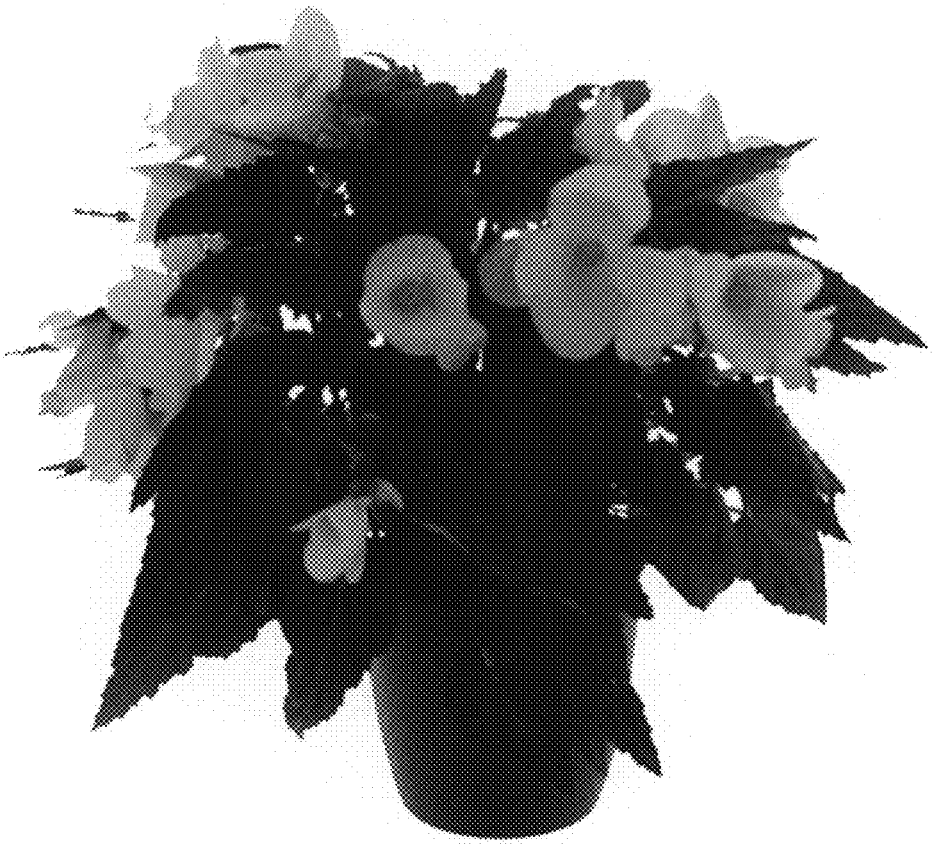

Botanical designation: *Begonia boliviensis* X *Begonia* x *tuberhybrida*.

Cultivar denomination: 'KROUTWH01'.

BACKGROUND OF THE INVENTION

The present invention relates to a new and distinct cultivar of *Begonia* plant, botanically known as *Begonia boliviensis* X *Begonia* x *tuberhybrida* and hereinafter referred to by the name 'KROUTWH01'.

The new *Begonia* plant is a product of a planned breeding program conducted by the Inventor in Ermelo, The Netherlands. The objective of the breeding program is to create new *Begonia* plants with uniform plant habit and numerous attractive flowers.

The new *Begonia* plant originated from a cross-pollination made by the Inventor in Ermelo, The Netherlands in September, 2015 of *Begonia boliviensis* 'Yagance', disclosed in U.S. Plant Pat. No. 19,817, as the female, or seed, parent with a proprietary selection of *Begonia* x *tuberhybrida* identified as code number KV11K1912-012, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in June, 2016.

Asexual reproduction of the new *Begonia* plant by terminal vegetative cuttings taken in a controlled greenhouse environment in Ermelo, The Netherlands since March, 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KROUTWH01'. These characteristics in combination distinguish 'KROUTWH01' as anew and distinct *Begonia* plant:

1. Broadly upright and mounded plant habit.
2. Moderately vigorous growth habit.
3. Moderately freely branching habit.
4. Dark green-colored leaves.
5. Large single-type white-colored flowers variably blushed with red purple that are positioned above and beyond the foliar plane.
6. Continuous flowering throughout the summer.

Plants of the new *Begonia* differ primarily from plants of the female parent, 'Yagance', in the following characteristics:

1. Plants of the new *Begonia* are more freely flowering than plants of 'Yagance'.
2. Plants of the new *Begonia* have larger and more open flowers than plants of 'Yagance'.

Plants of the new *Begonia* differ primarily from plants of the male parent selection in the following characteristics:

1. Plants of the new *Begonia* are more freely flowering than plants of the male parent selection.

2. Flowers of plants of the new *Begonia* are larger and more open than flowers of plants of the male parent selection.

Plants of the new *Begonia* can be compared to plants of *Begonia boliviensis* X *Begonia* x *tuberhybrida* 'KROUTOR01', disclosed in U.S. Plant Pat. No. 26,248. In side-by-side comparisons conducted in Ermelo, The Netherlands, plants of the new *Begonia* differed primarily from plants of 'KROUTOR01' in flower color as plants of the new *Begonia* have white-colored flowers blushed with red purple whereas plants of 'KROUTOR01' have dark orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'KROUTWH01' grown in a container.

Figure 2:
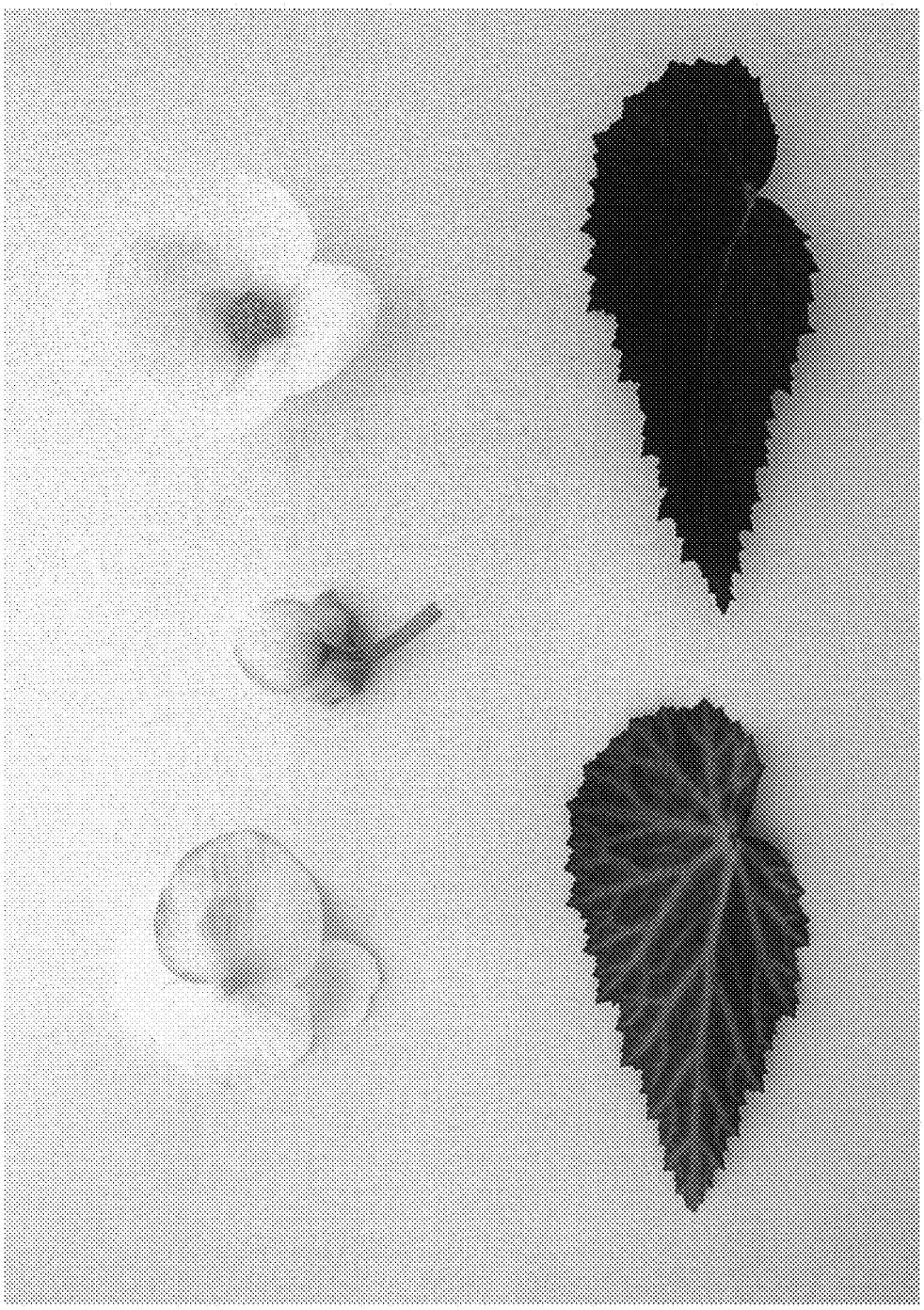

The photograph on the second sheet (FIG. 2 of 2) is a close up view of typical flowers and leaves of 'KROUTWH01'.

DETAILED BOTANICAL DESCRIPTION

The aforementioned photographs and following observations and measurements describe plants grown during the late spring and early summer in 10.5-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia boliviensis* X *Begonia* x *tuberhybrida* 'KROUTWH01'.

Parentage:

*Female, or seed, parent.*—*Begonia* x *tuberhybrida* 'Yagance', disclosed in U.S. Plant Pat. No. 19,817.

*Male, or pollen, parent.*—Proprietary selection of *Begonia* x *tuberhybrida* identified as code number KV11H1912-012, not patented.

Propagation:

*Type.*—By terminal vegetative cuttings.

*Time to initiate roots, summer and winter.*—About 20 days at temperatures about 20° C.

*Time to produce a rooted young plant, summer and winter.*—About five weeks at temperatures about 20° C.

*Root description.*—Fine, fibrous; typically white to orange brown in color, actual color of the roots is dependent on substrate composition, water quality, fertilizer type and formulation, substrate temperature and physiological age of roots.

*Rooting habit.*—Freely branching; medium density; plants of the new *Begonia* have not been observed to form tubers to date.

Plant description:

*Plant habit and form.*—Broadly upright and mounded plant habit; roughly globular in overall plant shape.

*Growth habit.*—Moderately vigorous growth habit and moderate growth rate; suitable for 9-cm and larger containers; under optimal environmental and cultural conditions, usually about eight weeks are required to produce proportional 10.5-cm potted plants from rooted cuttings.

*Branching habit.*—Moderately freely branching habit, about four basal branches each with about three secondary branches develop per plant; dense and bushy plant habit.

*Plant height, soil level to top of foliar plane.*—About 25.9 cm.

*Plant height, soil level to top of floral plane.*—About 26.3 cm.

*Plant width.*—About 33.9 cm.

*Lateral branches.*—Length: About 12.1 cm. Diameter: About 7 mm. Internode length: About 2.2 cm. Aspect: Erect to about 60° from vertical. Strength: Flexible, bending with the weight of the flowers. Texture and luster: Moderately pubescent; slightly glossy. Color, developing: Close to N199C. Color, developed: Slightly darker than 147A.

*Leaves.*—Arrangement: Alternate; simple. Length: About 13.4 cm. Width: About 5.8 cm. Shape: Narrowly ovate. Apex: Acute. Base: Oblique, lobes free. Margin: Dentate to serrate; slightly to moderately undulate. Texture and luster, upper surface: Sparsely to moderately pubescent; moderately velvety; slightly glossy. Texture and luster, lower surface: Sparsely to moderately pubescent; slightly velvety; slightly glossy to matte. Venation pattern: Pinnate. Color: Developing leaves, upper surface: Slightly darker than between 139A and N189A. Developing leaves, lower surface: Close to 183A to 183B. Fully expanded leaves, upper surface: Slightly darker than 139A; venation, close to 143B. Fully expanded leaves, lower surface: Close to 183C; venation, close to 146B to 146C; areas surrounding veins, close to 191B. Petioles: Length: About 5.3 cm. Diameter: About 4 mm. Texture and luster, upper and lower surfaces: Sparsely pubescent; glossy. Color, upper surface: Close to 177A; blotches, close to 185A. Color, lower surface: Close to between 177B and 200D. Stipules: Quantity and appearance: Two leafy stipules positioned at base of the leaf. Length: About 8 mm. Width: About 4.5 mm. Shape: Ovate. Apex: Acute. Base: Broadly cuneate. Margins: Ciliate. Color, upper and lower surfaces: Close to 145B.

Flower description:

*Flower form and flowering habit.*—Large single-type rotate flowers arranged in axillary cymes; typically about five flowers per cyme, numerous cymes in flower simultaneously and about 100 flowers developing per plant; flowers face upright to mostly outwardly and are positioned above and beyond the foliar plane.

*Natural flowering season.*—Plants flower continuously from the spring into the autumn in The Netherlands.

*Flower longevity*.—Individual flowers last about ten days on the plant; flowers not persistent.

*Fragrance*.—None detected.

*Inflorescence height*.—About 12.4 cm.

*Inflorescence diameter*.—About 8.1 cm.

*Flower buds*.—Length: About 2.4 cm. Diameter: Ranging from about 1 cm to 2.2 cm. Shape: Broadly ovate, flattened. Texture and luster: Smooth, glabrous; velvety; matte. Color: Close to 157B to 157D.

*Female flowers*.—Diameter: About 4.8 cm. Depth: About 3.3 cm. Shape: Rotate. Tepals: Quantity and arrangement: About five, or occasionally six, arranged in two whorls. Length, inner whorl: About 2.5 cm. Length, outer whorl: About 3.2 cm. Width, inner whorl: About 2 cm. Width, outer whorl: About 2.7 cm. Shape: Narrowly obovate to obovate. Apex: Obtuse. Base: Cuneate. Margin: Entire, not undulate. Texture and luster, upper surface: Smooth, glabrous; velvety; matte. Texture and luster, lower surface: Smooth, glabrous; velvety; slightly glossy. Color: When opening, upper surface: Close to NN155C; towards the base, close to 145C. When opening, lower surface: Close to NN155C; outer whorl of tepals slightly blushed with close to 65D; towards the base, close to 145C. Fully opened, upper surface: Close to NN155C slightly blushed with close to 65B; towards the base, close to 145C; venation, similar to lamina color; color does not change with development. Fully opened, lower surface: Close to NN155C moderately to strongly blushed with close to 62A and 65B to 65D; towards the base, close to 145C; venation, similar to lamina; color does not change with development. Tepaloids: None observed on female flowers.

*Male flowers*.—Diameter: About 5.5 cm. Depth: About 3 cm. Shape: Rotate. Tepals: Quantity and arrangement: About four arranged in two whorls. Length, inner whorl: About 3.5 cm. Length, outer whorl: About 3.9 cm. Width, inner whorl: About 2.4 cm. Width, outer whorl: About 4 cm. Shape: Narrowly obovate to obovate. Apex: Obtuse. Base: Cuneate. Margin: Entire, not undulate. Texture and luster, upper surface: Smooth, glabrous; velvety; matte. Texture and luster, lower surface: Smooth, glabrous; velvety; slightly glossy. Color: When opening, upper surface: Close to NN155C; towards the base, close to 157D. When opening, lower surface: Close to 157D; towards the base, close to 157B. Fully opened, upper surface: Close to NN155C occasionally blushed with close to 65D; towards the base, close to 157D; venation, similar to lamina color; color does not change with development. Fully opened, lower surface: Close to NN155C slightly to moderately blushed with close to 62A and 65B to 65D; venation, similar to lamina; color does not change with development. Tepaloids: None observed on male flowers.

*Flower bracts*.—Quantity and arrangement: Two positioned at the top of the peduncle. Length: About 1.4 cm. Width: About 1.3 cm. Shape: Broadly ovate. Apex: Obtuse. Base: Cuneate. Margin: Finely ciliate. Texture and luster, upper and lower surfaces: Smooth, glabrous; slightly glossy. Color, upper surface: Close to 145B. Color, lower surface: Close to 145B tinged with close to 179B.

*Peduncles*.—Length: About 6.4 cm. Diameter: About 5 mm. Angle: About 40° from lateral branch axis. Strength: Flexible, bending with the weight of the flowers. Texture and luster: Smooth, glabrous; moderately glossy. Color, upper and lower surfaces: Close to 152A to 152B.

*Pedicels*.—Length: About 2.6 cm. Diameter: About 2.5 mm. Angle: About 40° from peduncle axis. Strength: Flexible, bending with the weight of the flowers. Texture and luster: Smooth, glabrous; glossy. Color, upper and lower surfaces: Close to 145B to 145C.

*Reproductive organs*.—Stamens (present on male flowers only): Quantity per flower: About 90. Filament length: About 5 mm. Filament color: Close to 8B. Anther shape: Obovate; basifixed. Anther length: About 1 mm. Anther color: Close to 13A. Pollen amount: Scarce. Pollen color: Close to 4D. Pistils (present on female flowers only): Quantity per flower: About six, fused in pairs. Pistil length: About 6 mm. Style length: About 4 mm. Style color: Close to 150C. Stigma color: Close to 1A. Ovary color: Close to 150C.

*Seeds and fruits*.—To date, seed and fruit development have not been observed on plants of the new *Begonia*.

Disease & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KROUTWH01' as illustrated and described.

* * * * *